US00PP17114P2

(12) United States Plant Patent
Jonkers

(10) Patent No.: US PP17,114 P2
(45) Date of Patent: Sep. 26, 2006

(54) ***IMPATIENS* PLANT NAMED 'BUTLY LAVER'**

(50) Latin Name: ***Impatiens walleriana*×*Impatiens pseudoviola***
Varietal Denomination: Butly Laver

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 9 days.

(21) Appl. No.: 11/209,973

(22) Filed: Aug. 23, 2005

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Jondle & Associates P.C.

(57) ABSTRACT

An *Impatiens* cultivar particularly distinguished by lavender flowers, large leaves, and a trailing habit is disclosed.

1 Drawing Sheet

Genus and species: *Impatiens walleriana*×*Impatiens pseudoviola.*
Variety denomination: 'Butly Laver'.

BACKGROUND OF THE NEW PLANT

The present invention comprises a new and distinct cultivar of *impatiens,* botanically known as *Impatiens walleriana*×*Impatiens pseudoviola,* and hereinafter referred to by the cultivar name 'Butly Laver'. The new cultivar originated from a hybridization made in the year 2003 in Andijk, The Netherlands. The female parent was 'IY-639-1', an unpatented proprietary *impatiens* line having pink-colored flowers with eyes, while the male parent was 'SPZ-1-21', a lavender-flowered unpatented proprietary *impatiens* line.

The new cultivar was created in 2003 in Andijk, The Netherlands and has been asexually reproduced repeatedly by vegetative cuttings and tissue culture in Gilroy, Calif. and Andijk, The Netherlands over a one and a half year period. The plant has also been trialed at Gilroy, Calif., Litchfield, Mich. and Andijk, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Andijk, The Netherlands.

1. Lavender-colored flowers;
2. Floriferous; and
3. A trailing habit.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of three four and one half month-old plants grown in an 8-inch pot in Andijk, The Netherlands in a greenhouse in a late winter/spring trial setting.

The accompanying photograph shows overall plant habit including blooms, buds and foliage; the inset shows mature inflorescences.

DESCRIPTION OF THE NEW CULTIVAR

The following detailed descriptions set forth the distinctive characteristics of 'Butly Laver'. The data which defines these characteristics were collected from asexual reproductions carried out in Gilroy, Calif. The plant history was taken on 12-week-old plants grown in 4-inch pots in a poly-covered greenhouse in the spring/early summer season. Color readings were taken under natural light in the greenhouse. Color references are primarily to The R.H.S. Colour Chart of The Royal Horticultural Society of London (R.H.S.) (2001). Texture description details were observed under a dissecting microscope.

DETAILED BOTANICAL DESCRIPTION

Classification:
- *Botanical.*—*Impatiens walleriana*×*Impatiens pseudoviola.*
- *Common name.*—*Impatiens.*

Parentage:
- *Female parent.*—'IY-639-1' proprietary line (unpatented).
- *Male parent.*—'SPZ-1-21' proprietary line (unpatented).

Growth:
- *Form.*—Slightly upright and semi-trailing.
- *Growth and branching habit.*—Good branching and moderately vigorous; pinching of the terminal apices enhances branching and floriferousness.
- *Height (from soil level to top of blooms).*—10–15 cm.
- *Width (including flowers).*—20–30 cm.
- *Time to produce a finished flowering plant.*—8–10 weeks for a 4-inch pot.
- *Outdoor plant performance.*—Does well in afternoon shade; is free-flowering through the spring, summer and fall; has some heat tolerance; use in hanging baskets, mixed containers, and window boxes.

*Time to initiate and develop roots.*—10–21 days.
*Root description.*—Fibrous, fleshy, and white.

Leaves:
*Arrangement.*—Alternate, whorls.
*Length.*—3.5–3.7 cm.
*Width.*—3.0–3.3 cm.
*Shape.*—Ovate.
*Margin.*—Crenate with one ciliate at each lobe.
*Apex.*—Acute.
*Base.*—Attenuate.
*Color.*—Upper surface: Closest to RHS 147A. Lower surface: RHS 147B.
*Texture.*—Glabrous.
*Venation.*—Pinnate.
*Venation color.*—RHS 144B.
*Petiole.*—Length: 1.0–1.5 cm. Diameter: 0.15–0.2 cm. Color: RHS 144B. Texture: Glabrous.

Stems:
*Length.*—10–15 cm.
*Diameter.*—0.4–0.5 cm.
*Internode length.*—1.0–2.0 cm.
*Color.*—RHS 144B.
*Texture.*—Glabrous.
*Stem anthocyanin.*—Present as a slight hue in small irregular blotches, reddish brown.
*Pedicel.*—Length: 1.5–2.5 cm. Diameter: 0.1 cm. Color: RHS 144B. Texture: Glabrous.
*Peduncle.*—Length: 2.2–2.5 cm. Diameter: 0.1 cm. Color: RHS 144B. Texture: Glabrous.

Flower buds:
*Shape.*—Ovate.
*Length.*—0.5–0.8 cm.
*Diameter.*—0.4–0.5 cm.
*Color at tight bud.*—RHS 69D.

Inflorescence:
*Blooming habit.*—Continuous and freely all through the spring, summer and fall.
*Inflorescence type.*—Racemes in leaf axis and in leaf whorls.
*Number of flowers per raceme and/or whorl.*—Approximately 10–15, including buds.
*Number of flowers per plant.*—Approximately 75–100.
*Lastingness of individual blooms on the plant.*—4–8 days.
*Fragrance.*—None.

Flowers:
*Floret form.*—5 petals, 1 standard or dorsal (free); 2 lateral or lobed pairs (wing petals), deeply lobed.
*Floret diameter.*—2.7–3.0 cm.
*Floret height.*—2.6–2.8 cm.
*Color, immature flowers, upper surface.*—Dorsal petal: Shades of RHS 76B and RHS 76C with a small spot of RHS 145B at the apex. Lateral petal: Between RHS 76B and RHS 76C with RHS 77A blotches on the basal one-third of the petal.
*Color, immature flowers, lower surface.*—Dorsal petal: RHS 76D. Lateral petal: RHS 76D.
*Color, mature flowers, upper surface.*—Dorsal petal: RHS 76C, but lighter with a small spot of RHS 145B at the apex. Lateral petal: RHS 76C with RHS 77A blotches on the basal one-third of the petal.
*Color, mature flowers, lower surface.*—Dorsal petal: RHS 76D. Lateral petal: RHS 76D.

Petals:
*Quantity.*—5.
*Dorsal.*—Length: 1.1–1.2 cm. Width: 1.7–1.8 cm. Shape: Orbicular. Apex: Emarginate. Base: Fused. Margin: Entire. Texture: Papillose.
*Lateral.*—Length: 1.4–1.5 cm. Width: 0.7–1.1 cm. Shape: Spathulate. Apex: Emarginate. Base: Fused. Margin: Entire. Texture: Glabrous.

Sepals:
*Quantity.*—3, 1 larger than the others, with a spur.
*Large sepal.*—Color: RHS 145C with a slight RHS 145B veining; RHS 144A keel. Length: 1.0–1.2 cm. Width: 0.8–1.1 cm. Shape: Broadly elliptical. Apex: Acute. Base: Fused. Margin: Entire. Texture: Glabrous. Spur: Color: RHS 145C with slight anthocyanin blotches, RHS 56D, distally and a 1.0 mm tip of RHS 144A. Length: 0.3 cm.
*Small sepal.*—Color: RHS 144A. Length: 0.3 cm. Width: 0.1 cm. Shape: Linear. Apex: Acute. Base: Fused. Margin: Entire. Texture: Glabrous.

Reproductive organs:
*Stamens.*—5; more or less fused by the anthers and covering the ovary.
*Pollen cap color.*—RHS 75C.
*Pollen amount.*—Not observed.
*Pistil.*—1, complete.

Fruit and seed set: Has not been observed.
Disease and insect resistance: Has not been observed.

COMPARISON WITH KNOWN CULTIVARS

'Butly Laver' differs from the female parent, 'IY-639-1' proprietary line (unpatented), in that 'Butly Laver' has smaller flowers with a lavender color and a more trailing habit than 'IY-639-1'. 'Butly Laver' differs from the male parent, 'SPZ-1-21' proprietary line (unpatented), in that 'Butly Laver' has larger flowers and is more floriferous than 'SPZ-1-21'.

'Butly Laver' differs from the commercial cultivar 'Fify Lav' (U.S. Plant Pat. No. 11,821) in that 'Butly Laver' is a larger plant with a more trailing habit, has larger leaves, and has a larger, lighter lavender flower color than 'Fify Lav'.

I claim:

1. A new and distinct cultivar of *Impatiens* plant as shown and described herein.

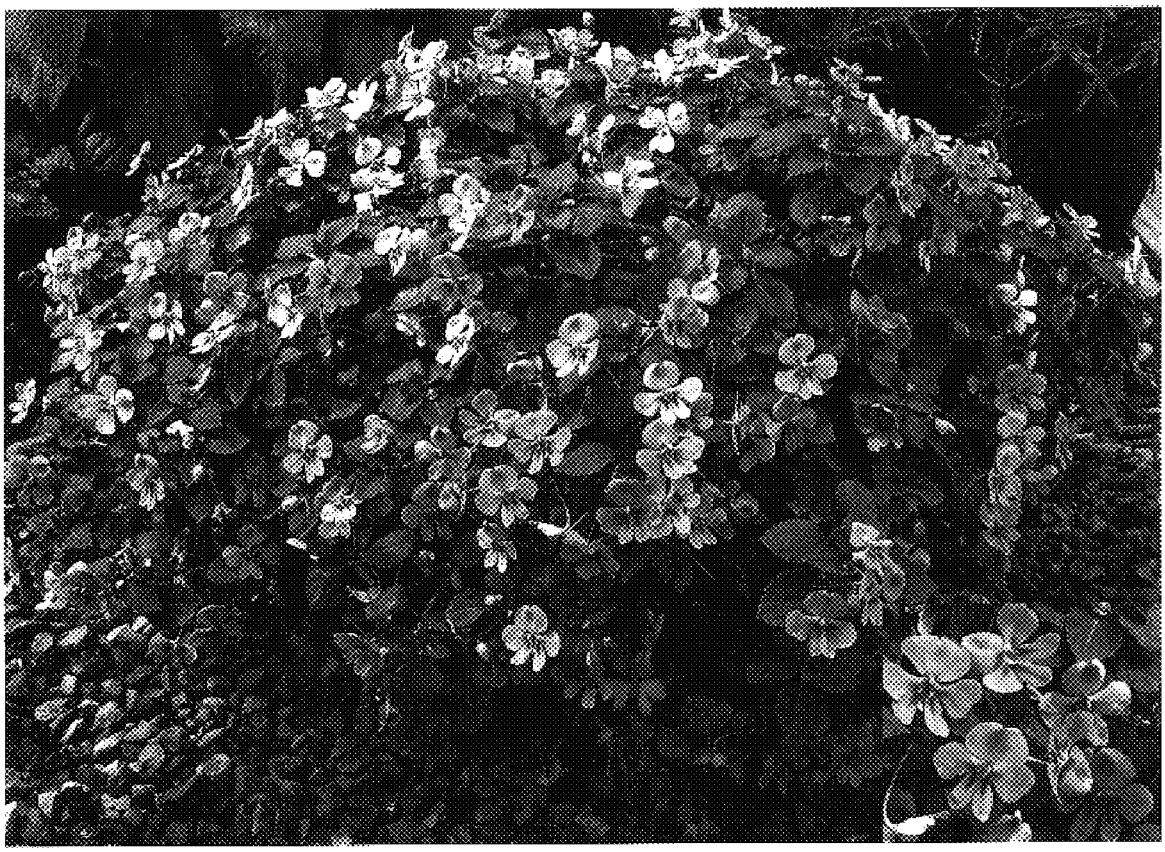

* * * * *